(12) United States Patent
Wanner et al.

(10) Patent No.: US 7,579,193 B2
(45) Date of Patent: Aug. 25, 2009

(54) METHOD AND DEVICE FOR CHARACTERIZING OSI MATERIAL

(75) Inventors: Thomas Wanner, Schwebenhausen (DE); Norbert Rodler, Zolling (DE); Klaus Rieblinger, Zolling (DE); Thomas Hubensteiner, Freising (DE)

(73) Assignee: Fraunhofer-Gesellschaft zur Förderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 10/590,971

(22) PCT Filed: Jan. 31, 2005

(86) PCT No.: PCT/EP2005/001099

§ 371 (c)(1),
(2), (4) Date: Nov. 13, 2006

(87) PCT Pub. No.: WO2005/085836

PCT Pub. Date: Sep. 15, 2005

(65) Prior Publication Data

US 2007/0191524 A1    Aug. 16, 2007

(30) Foreign Application Priority Data

Feb. 26, 2004    (DE) .................. 10 2004 009 870

(51) Int. Cl.
*C08K 5/06* (2006.01)
*B01D 53/047* (2006.01)
(52) U.S. Cl. .................. 436/127; 436/136; 422/78
(58) Field of Classification Search .............. 436/136, 436/127; 422/80; 95/12
See application file for complete search history.

(56) References Cited

U.S. PATENT DOCUMENTS

| 4,947,339 | A | | 8/1990 | Czekajewski et al. |
| 5,358,876 | A | * | 10/1994 | Inoue et al. ................. 436/136 |
| 5,473,162 | A | * | 12/1995 | Busch et al. ............. 250/341.6 |
| 5,906,672 | A | * | 5/1999 | Michaels et al. ............... 95/12 |
| 6,455,620 | B1 | | 9/2002 | Cyr et al. |
| 2002/0068017 | A1 | * | 6/2002 | Naatz et al. ................... 422/80 |
| 2003/0082321 | A1 | | 5/2003 | Kennedy et al. |
| 2003/0183801 | A1 | * | 10/2003 | Yang et al. ............. 252/188.28 |

FOREIGN PATENT DOCUMENTS

DE 19528400 10/1996
WO PCT/EP2005/001099 7/2005

OTHER PUBLICATIONS

Rieblinger, Klaus. Quality Advantages, Oxygen-Depleting Packaging Against Undesired Oxidation Reactions, May 2003, Lebensmitteltechnik.Online.DE, pp. 66-67. (Machine Translation, Oct. 2007).*

* cited by examiner

*Primary Examiner*—Walter D Griffin
*Assistant Examiner*—Christine T Mui
(74) *Attorney, Agent, or Firm*—Mathew B. Deriner, Esq.; Gibson & Dernier LLP

(57) ABSTRACT

Methods and apparatus for characterising OSI-materials provide for: introducing the material into a measurement cell; subjecting the material to a gas mixture containing oxygen; permitting a certain time or at certain time interval or intervals to elapse; measuring a defined volume part of the gas mixture with regard to its oxygen concentration using a measurement circuit, which together with the time component represents a characterisation of the OSI-material, wherein the OSI-material in the measurement cell is subjected to the gas mixture circulated in a closed reaction circuit, and the defined volume part is conveyed into a measurement circuit containing a gas, for the measurement of the oxygen concentration.

10 Claims, 4 Drawing Sheets

US 7,579,193 B2

METHOD AND DEVICE FOR CHARACTERIZING OSI MATERIAL

BACKGROUND

The invention relates to a device for characterising OSI-material in which the material is subjected to a gas mixture containing oxygen and then volume part of the gas mixture is measured with regard to its oxygen concentration.

Various analytic apparatus and methods for characterising $O_2$-scavengers falling under the term of OSI-materials are known. In gas chromatography for example, a certain quantity of an $O_2$-scavenger is subjected to a gas mixture which contains oxygen. After a certain time in which the $O_2$-scavenger breaks down the oxygen from the gas mixture, a certain quantity of the present gas mixture is lead to a measurement apparatus, in which the gas to be analysed is separated from the gas mixture via a separating column, and is quantified via a detector, e.g. a helium pulsed-discharged-detector.

Furthermore, electrochemical methods, using e.g. $O_2$-sensitive electrodes are known, which detect the oxygen change in a compartment via an electrochemical reaction. There are also pressure measurement methods with which the pressure change in a rigid compartment is detected via a pressure sensor. Thereby, the pressure change is directly proportional to the oxygen change caused by the $O_2$ scavenger. Furthermore, fluorescence measurement technology may be applied, with which the fluorescence quenching of an actively excited, $O_2$-sensitive dye is detected. The fluorescence quenching is indirectly proportional to the oxygen concentration.

At present, no special measurement technology exists for characterising $O_2$-indicators, which likewise represent an OSI-material.

$O_2$-scavengers are substances which absorb and/or adsorb the oxygen. The systems which have established themselves on the market today may be primarily classified according to the $O_2$-scavenger substrate and according to their initialisation mechanism. With the classification by way of the $O_2$-scavenger substrate, one differentiates according to inorganic $O_2$-scavengers, e.g. iron-based or sulphite-based systems, according to low-molecular organic $O_2$ scavengers, e.g. ascorbate-based systems, and according to high-molecular organic $O_2$-scavengers, e.g. polyolefin-based or polyamide-based systems. The $O_2$-scavengers are either UV-initialised or humidity-initialised. This means that the $O_2$-scavenger function is only present after an exposure to UV-light or humidity.

Indicator systems may generally be divided into time-temperature indicator systems (TTI), gas/leakage indicator systems and freshness indicator systems. Time-temperature indicators integrate the time-temperature history of a product and thus provided direct information on its storage conditions. The indicator effect is effected by way of a chemical reaction or by way of counter-diffusion of two dyes. Gas/leakage indicators detect the gas concentration, e.g. $O_2$, $CO_2$ or $H_2O$ in the packaging space of a product. They thus provide indirect information on the quality of the product. The indicator effect is caused by a chemical reaction with the respective gas as a reactant. Freshness indicators detect the metabolism products of micro-organisms and thus provide direct information on the quality of the product. The indicator effect is caused by a chemical reaction of the metabolism products. All mentioned indicator systems represent their indicator effect by way of a visible colour change.

OSI-materials, specifically $O_2$-scavengers, $O_2$ indicators or $O_2$-scavenger/$O_2$-indicator systems are applied in the foodstuff industry, pharmaceutics industry, electronics industry, chemical industry, and with other applications. In order to be able to adapt these OSI-materials in their quantity, their effect and other parameters, to the demands of the respect set aims, it is necessary to characterise the respective OSI-material, wherein the basis of the characterisation is the oxygen concentration with regard to a time component.

SUMMARY OF THE INVENTION

It is therefore the object of the invention to provide a method and a device for characterising OSI-materials, with which one may characterise OSI-materials, including $O_2$-indicators, in a relatively simple manner and with a great sensitivity.

According to the invention, this object is achieved by the characterising features of the main claim as well as of the auxiliary claim, in combination with their preambles.

The oxygen concentration may be measured in a sensitive manner by way of the fact that OSI-material is accommodated in a measurement cell, which in a closed reaction circuit is subjected to a gas mixture containing oxygen, and a defined volume part is conveyed into a measurement circuit containing gas for measuring the oxygen concentration. Very small concentrations may detected in an effective manner by way of the closed reaction circuit. The corresponding device is constructed in a simple manner and is easily handled.

Advantageous further formations and improvements are possible by way of the measures specified in the dependent claims.

It is particularly advantageous that humidity may be led to the closed reaction circuit via an external humidification unit, by way of which the $O_2$-scavenger may be initialised. A characterisation of the $O_2$-scavenger may be carried out at any relative humidity by way of this.

By way of the provision of a measurement cell which is transparent for the given wavelength regions, e.g. UV/VIS or visible light, the $O_2$-scavenger contained in the measurement cell may be subjected to UV-radiation and be initialised by way of this.

With the provision of an $O_2$-indicator and/or an $O_2$-scavenger/$O_2$-indicator system, one may measure its colour or colour change which are used for the characterisation of the $O_2$-indicator or of the system.

Very low leakage rates are to be noted by way of the fact that the components of the reaction circuit and particularly of the measurement circuit are encapsulated, by which means very low concentrations, e.g. between 20 and 0% oxygen may be measured.

By way of incorporating complete packaging and drinks bottles which contain OSI-materials, these may be characterised in a complete manner. Advantageously, the measurement circuit is likewise a closed circuit, and the reaction circuit and the measurement circuit are connected to one another via a sample loop which may be switched into the respective circuit. By way of this, one may convey a defined volume share from the reaction circuit into the measurement circuit in a simple manner.

BRIEF DESCRIPTION OF THE DRAWINGS

One embodiment example of the invention is represented in the drawing and is explained in more detail in the subsequent description. There are shown in.

DETAILED DESCRIPTION OF THE INVENTION

Figure 1:
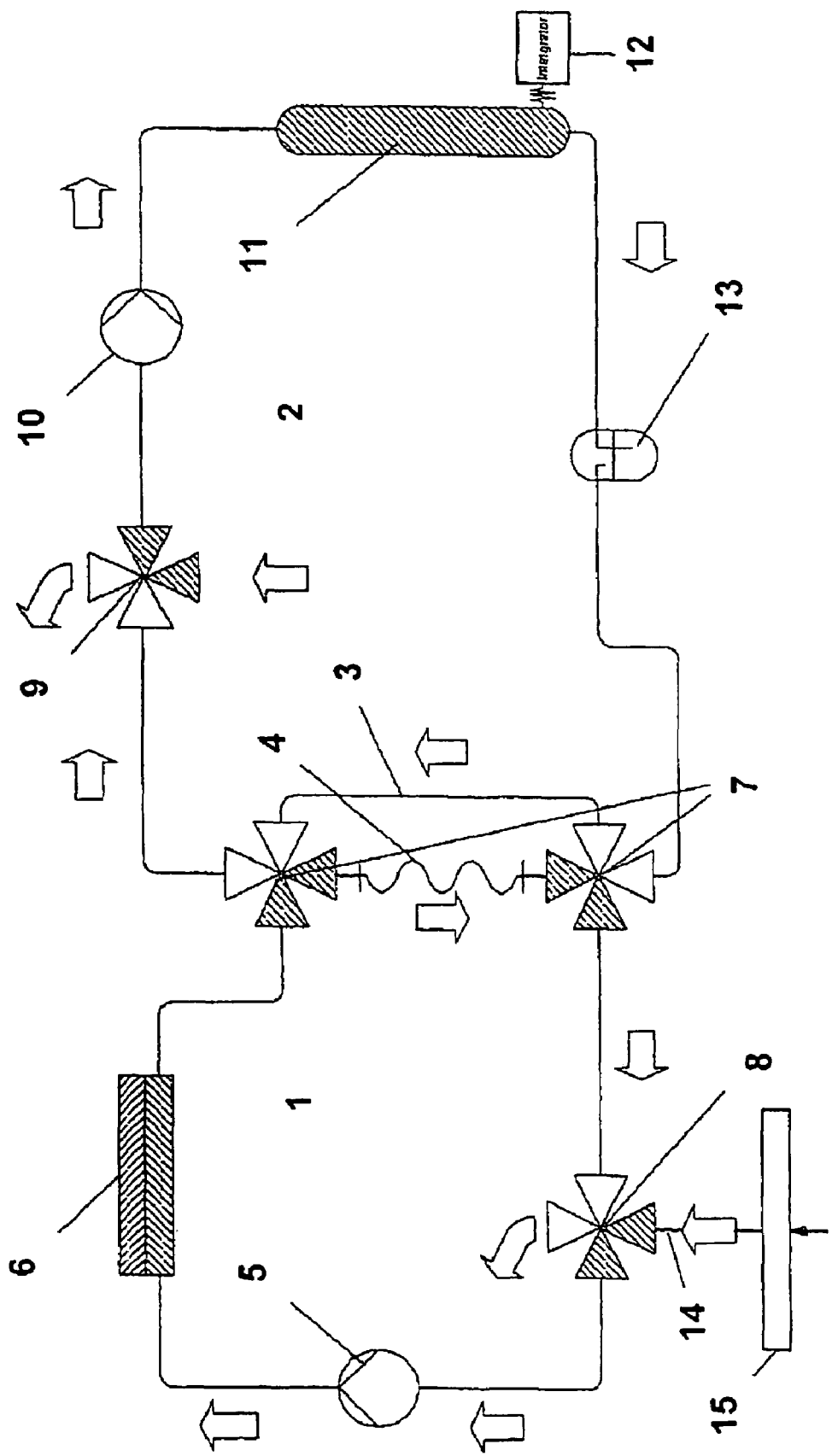
FIG. 1 illustrates the schematic representation of the device according to the invention in a first method condition.
Figure 2:
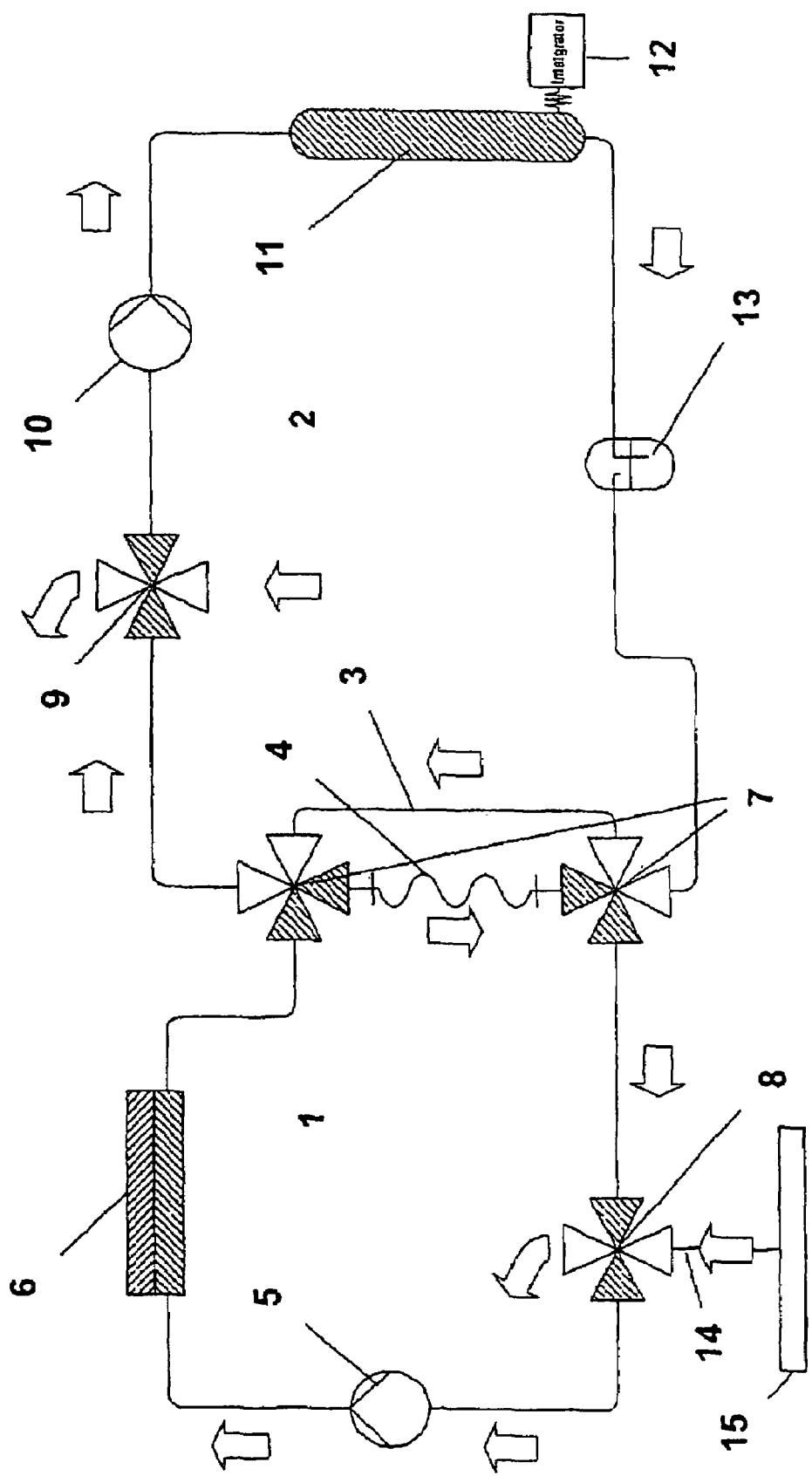
FIG. 2 illustrates the device according to FIG. 1 in a second method condition.
Figure 3:
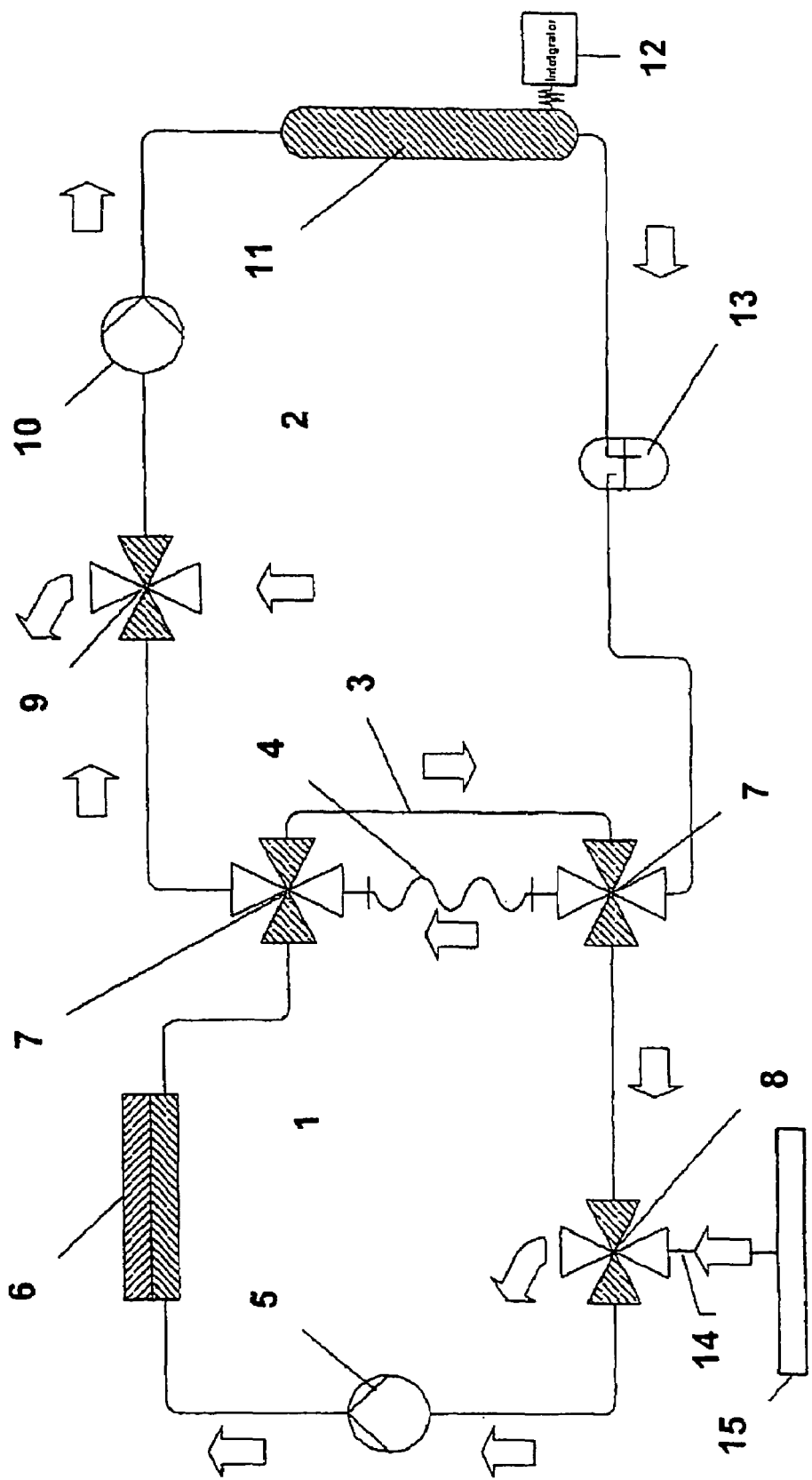
FIG. 3 illustrates the device according to FIG. 1 and FIG. 2 in a third method condition.

The device according to the invention for characterising OSI-material is schematically shown in the FIGS. 1 to 3, wherein the different figures represent different method flow conditions. The device consists of a reaction circuit 1 and a measurement circuit 2. A first switch-over branch and/or circuit 3 and a second switch-over branch which is indicated a sample loop 4 may be switched in each case between the reaction circuit 1 and the measurement circuit 2.

The reaction circuit 1 forms a closed reaction circulation and consists of a pump 5, of a transparent measurement cell 6 or one which is transparent for selected wavelength regions, of the sample loop 4 or the switch-over branch and/or circuit 3, of a 6-way valve 7 which is represented as a simulated 6-way valve (equivalent circuit diagram of two 4-way valves and switch-over branch) and switches between the sample loop 4 and the switch-over branch and/or circuit 3, and of a 4-way valve.

The measurement circuit 2 in the shown embodiment example is likewise designed as a closed circuit, and in other embodiments it is conceivable for the measurement circuit to be an open circuit or branch. The measurement circuit comprises a 4-way valve 9 for the removal, the supply and the switching-through of a gas flow, a pump 10, an oxygen-sensitive sensor arrangement 11 which for example may comprise a Mocon-sensor or a Coulox-sensor which are based on an electrochemical principle (the Mocon-sensor builds up a potential difference by way of electrochemical procedures on contact with oxygen, wherein this physical variable is correlated to the oxygen concentration), an evaluation unit 12 which is in connection with the sensor arrangement 11 and e.g. may comprise an integrator, and a humidification unit 13. As already mentioned above, the 6-way valve 7 which may be switched between the sample loop 4 and the switch-over branch and/or circuit 3, is also a constituent of the measurement circuit 2.

The 4-way valve 8 of the reaction circuit 1 likewise serves for the supply, the removal and the switching-through of a gas flow, wherein a supply conduit 14 is connected to an external humidification unit 15.

The shown device or the analytical apparatus permits a characterisation of pure OSI-materials (e.g. substances in powder form), but also of OSI-materials which are incorporated into different matrices, e.g. polymers. The formation of the matrix may be realised in the form of the actual packages (e.g. foils in mono-layer- or multi-layer constructions) and drinks bottles.

The OSI-material to be characterised, which in the following example is to be an $O_2$-scavenger, is introduced into the measurement cell 6. Subsequently, the complete reaction circuit is flushed with an $O_2/N_2$-gas flow which for example may contain 20% oxygen and 80% nitrogen and which is supplied via the 4-way valve 8. This means that the supplied, defined gas flow, delivered by the pump 5, flows through the measurement cell 6, the sample loop 4 which is switched into the reaction circuit via the 6-way valve, and is led away via the 4-way valve 8, until the complete reaction circuit, apart from the defined gas flow, no longer contains any foreign gas. This is represented in FIG. 1, wherein the "bright" arrows represent the foreign gas to be led away. As the case may be, with the pump switched off, the defined gas flow may be supplied by way of the excess pressure of the gas bottle, wherein the throughput speed is set by way of a flow-meter.

If, with regard to the $O_2$-scavenger, it is the case of a humidity-initialising $O_2$-scavenger, then the defined gas flow supplied via the 4-way valve is previously led through the external humidification unit 15 and subjected to the required relative humidity, in order to initialise the $O_2$-scavenger contained in the measurement cell.

In the case of a UV-initialising $O_2$-scavenger, the measurement cell 6 must be transparent at least to the UV-radiation, and a UV-radiation source which is not shown and which irradiates and thus initialises the scavenger, is allocated to the measurement cell.

After the reaction circuit 1 has been adequately flushed, the 4-way valve 8 is switched over, and the gas quantity introduced at this point in time is circulated in the reaction circuit with the help of the pump 5. This may be recognised in FIG. 2.

A nitrogen gas flow, preferably 100% nitrogen, is led via the 4-way valve 9 to the measurement circuit 2 and led further by the pump 10, wherein the 6-way valve 7 switches the switch-over branch and/or circuit 3 into the measurement circuit 2. Foreign gas is led out of the measurement circuit 2 via the 4-way valve 9, which is indicated by the white arrows. When the foreign gas has been completely led away, the 4-way valve 9 is switched in a manner such that the introduced gas quantity is circulated in the measurement circuit with the help of the pump 10. This is represented in FIG. 2. The humidification unit 13 exclusively has the task of humidifying the oxygen-sensitive sensor of the sensor arrangement 11.

The oxygen content of the circulated gas changes in the reaction circuit on account of the $O_2$-sorption of the $O_2$-scavenger material accommodated in the measurement cell 6. The sample loop 4 is switched from the reaction circuit 1 into the measurement circuit via the 6-way valve at certain time intervals, e.g. at intervals of 24 hours, for determining the oxygen concentration. This is represented in FIG. 3. By way of switching the 6-way valve, a defined volume part is conveyed from the reaction circuit 1 into the measurement circuit 2, and the oxygen contained in the defined volume part is detected with the help of the sensor arrangement 11. The evaluation unit 12 which contains an integrator, then determines the oxygen concentration of the reaction circuit whilst using the gas quantities contained in the reaction circuit 1 and in the measurement circuit 2. The aliquote volume part which is conveyed from the reaction circuit 1 into the measurement circuit 2 leads to a signal (surface signal) at the sensor 11. This corresponds to a certain oxygen concentration in the reaction circuit. This means that a certain oxygen concentration in the circuit is assigned to the sensor signal.

Figure 4:
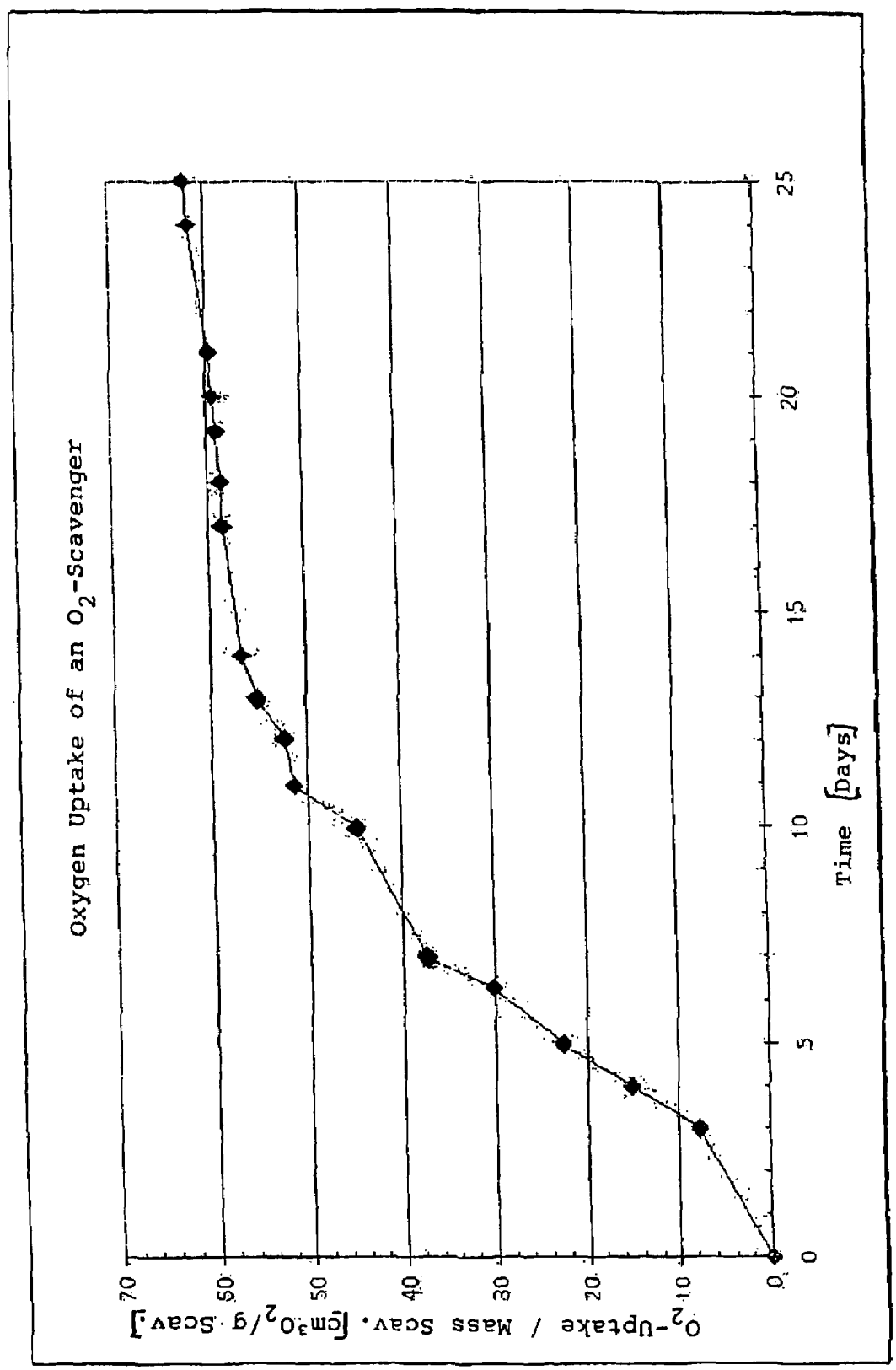
FIG. 4a illustrates characteristic line of the oxygen uptake of an $O_2$-scavenger in dependence on time, which serves for characterising the material.

The characterisation of the material of the $O_2$-scavenger used in this embodiment example is based on the evaluation of the capacity and kinetics. This means that the evaluation unit for example, whilst using the quantity of the $O_2$-scavenger accommodated in the measurement cell 6, determines its oxygen uptake over time. Such a characteristic line is represented in FIG. 4, with which the ordinate represents the oxygen reduction with respect to the mass of the scavenger, and the abscissa represents the time in days. Usually, the related oxygen breakdown value present at the end of the measurement sequence is indicated as the capacity, and the kinetics are expressed in a simplified manner by the gradient of the characteristic line.

One proceeds in a corresponding manner for the characterisation of an $O_2$-indicator. The $O_2$-indicator is introduced into the measurement cell, and in each case the complete reaction circuit is flushed with a defined $O_2/N_2$ gas flow via the 4-way valve 8. Depending on the type of initialisation, either the indicator is initialised via the gas flow subjected to humidity or via UV-irradiation via the UV-transparent measurement cell 6. Subsequently, the introduced gas quantity is circulated in the reaction circuit 1 with the help of the pump 5.

The measurement circuit 2, as described above is flushed with an $N_2$ gas flow via the 4-way valve 9. Subsequently, the introduced gas quantity is circulated in the measurement circuit with the help of the pump 10 (see FIG. 2). The sample loop 4 is switched from the reaction circuit 1 into the measurement circuit 2 via the 6-way valve 7 at certain time intervals, e.g. 24 hours (FIG. 3), for determining the oxygen concentration in the reaction circuit 1. By way of this transfer of an aliquote or defined volume part from the reaction circuit 1 into the measurement circuit, the respective $O_2$-concentration of the reaction circuit present at that point in time is detected and determined with the help of the oxygen-sensitive sensor 11 and the evaluation unit 12.

At the points in time in which the oxygen content is measured, the colour or the colour change of the $O_2$-indicator material in the measurement cell is ascertained or measured. For example, a colour measurement apparatus or a photometer or likewise, which is placed onto the transparent measurement cell, may be allocated to the measurement cell. A further possibility is a colour comparison with a colour scale.

For characterising the $O_2$-indicator, the colour change of the indicator over the oxygen concentration time interval or the oxygen (concentration) threshold value is used. For this, the evaluation unit determines the integral of the $O_2$-concentration over time. The indicator for example changes its colour from colourless to green when it has detected a certain quantity of oxygen (e.g. 0.5 hours, 21% $O_2$ or 1 hour 10% $O_2$).

Of course, a characterisation of an $O_2$-scavenger/indicator system may be implemented in a corresponding manner, wherein the scavenger and indicator may be admitted into the measurement cell 6 mixed or separated. Additionally to the characterisation variables already specified, there exists the possibility of determining a colour change of the $O_2$-indicator in dependence on the residual capacity of the $O_2$-scavenger.

The $O_2$-scavenger sorbs the oxygen. Its absolute capacity is 60 $cm^3/g_{scav}$ (see FIG. 4). With an achieved capacity for example of 45 $cm^3/g_{scav}$, the indicator changes its colour from colourless to green, and indicates to the user that the $O_2$-scavenger still has a residual capacity of 15 $cm^3/g_{scav}$.

With the characterisation of foodstuff packaging or drinks bottles which mostly consist of several polymeric layers (multi-layer construction), and one of the layers contains the OSI-material, the packaging may assume the place of the measurement cell (packaging is a closed compartment). This means that the lid is removed from the measurement cell and the packaging is connected to the supply and discharge openings of the measurement cell via conduits. In this case the packaging is thus the measurement cell. This characterisation is particularly realistic since the oxygen entering the packaging from the surroundings is likewise detected.

One may also determine the trigger mechanism of OSI-materials with the device. This concerns a combined $O_2$-scavenger/indicator system (OSI), and $O_2$-scavenger system (OS) and $O_2$-indicator system (OI). With a humidity-triggered system, the relative humidity in the gas flow is successively increased via the humidification unit. By way of this, one determines that relative humidity, above which the system is activated. With an OS- or OSI-system, the activation is shown by the reduction of the $O_2$-concentration. With an OS- or OSI-system, the activation is indicated by the colour change of the system. With a UV-triggered system, the intensity of the radiation or the wavelength range is successively increased. The further procedural manner is identical to the humidity-triggered system.

The invention claimed is:

1. A device for characterising OSI-materials, comprising:
   a closed reaction circuit having a device for supplying a gas flow containing oxygen, a pump for delivery of the gas flow, and a measurement cell for receiving the OSI-material; and
   a closed measurement circuit having a device for supplying a gas flow, a pump for delivery of the gas flow and a sensor arrangement for detecting oxygen, and an evaluation unit,
   wherein a sample loop with a defined volume is arranged in the closed reaction circuit, which for conveying the defined volume of the gas flow of the reaction circuit is operable to be switched into the closed measurement circuit from the closed reaction circuit, and the sample loop is operable to be switched into the closed reaction circuit from the closed measurement circuit.

2. The device according to claim 1, wherein the measurement circuit is a closed measurement circuit and comprises a device for the supply of the gas flow, a pump for delivery of the gas flow, wherein a part of the reaction circuit, with the defined volume, may be switched into the measurement circuit via valves.

3. The device according to claim 2, wherein the measurement circuit comprises a switch-over branch which may be switched into the reaction circuit via the valves when the part of the reaction circuit with the defined volume is switched into the measurement circuit.

4. The device according to claim 1, wherein the sensor arrangement contains at least one oxygen-sensitive sensor, and the evaluation unit contains an integrator.

5. The device according to claim 1, wherein the device for the supply of the gas flow containing oxygen into the reaction circuit is connected to a humidification unit, which subjects the gas flow to a humidification for the initialisation of the material in the measurement cell.

6. The device according to claim 1, wherein the measurement cell is transparent to settable wavelength regions.

7. The device according to 6, wherein a UV-radiation source which irradiates the material for its initialisation, is allocated to the measurement cell.

8. The device according to claim 1, further comprising a device for measuring the colour and/or the colour change of the material allocated to the measurement cell.

9. The device according to claim 1, wherein the reaction circuit comprises a sample loop containing the defined volume part, which may be switched into the measurement circuit via multi-way valves.

10. The device according to claim 1, wherein the components of the reaction circuit and of the measurement circuit are encapsulated.

* * * * *

UNITED STATES PATENT AND TRADEMARK OFFICE
CERTIFICATE OF CORRECTION

PATENT NO. : 7,579,193 B2
APPLICATION NO. : 10/590971
DATED : August 25, 2009
INVENTOR(S) : Thomas Wanner et al.

It is certified that error appears in the above-identified patent and that said Letters Patent is hereby corrected as shown below:

Title page, item (75): "Thomas Wanner, Schwebenhausen, DE" should be --Thomas Wanner, Schrobenhausen, DE--; and "Klaus Rieblinger, Zolling, DE" should be --Klaus Rieblinger, Hallbergmoos, DE--.

Signed and Sealed this

Twenty-seventh Day of October, 2009

David J. Kappos
*Director of the United States Patent and Trademark Office*